United States Patent
Ishikawa et al.

(10) Patent No.: US 6,497,714 B1
(45) Date of Patent: Dec. 24, 2002

(54) ULTRASONIC TROCAR

(75) Inventors: Manabu Ishikawa; Mitsumasa Okada, both of Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/350,671

(22) Filed: Jul. 9, 1999

(30) Foreign Application Priority Data

Jul. 16, 1998 (JP) ............................................. 10-201964
Apr. 1, 1999 (JP) ............................................. 11-095112

(51) Int. Cl.$^7$ ............................................. A61B 17/32
(52) U.S. Cl. ........................................................ 606/169
(58) Field of Search ........................... 606/1, 184, 185, 606/169; 604/22, 164, 264

(56) References Cited

U.S. PATENT DOCUMENTS

| | | |
|---|---|---|
| 4,545,374 A | 10/1985 | Jacobson |
| 5,123,903 A | 6/1992 | Quaid et al. |
| 5,263,937 A | 11/1993 | Shipp |
| 5,267,965 A | 12/1993 | Deniega |
| 5,314,417 A | 5/1994 | Stephens et al. |
| 5,342,380 A | 8/1994 | Hood |
| 5,359,996 A | 11/1994 | Hood |
| 5,405,328 A * | 4/1995 | Vidal et al. ................. 606/158 |
| 5,445,142 A | 8/1995 | Hassler, Jr. |
| 5,449,370 A * | 9/1995 | Vaitekunas .................. 606/169 |
| 5,472,447 A | 12/1995 | Abrams et al. |
| 5,569,292 A * | 10/1996 | Sewemberger et al. ...... 606/169 |
| 5,599,347 A * | 2/1997 | Hart et al. .................. 604/264 |
| 5,674,237 A * | 10/1997 | Ott ............................. 606/185 |
| 5,676,156 A * | 10/1997 | Yoon .......................... 606/184 |
| 5,728,130 A | 3/1998 | Ishikawa et al. |
| 5,776,112 A | 7/1998 | Stephens et al. |
| 5,904,699 A * | 5/1999 | Schwemberger et al. ... 606/185 |
| 5,989,274 A * | 11/1999 | Davison et al. ............. 606/169 |
| 6,063,099 A * | 5/2000 | Danks et al. ............... 606/185 |

* cited by examiner

*Primary Examiner*—Michael J. Milano
*Assistant Examiner*—(Jackie) Tan-Uyen T. Ho
(74) *Attorney, Agent, or Firm*—Frishauf, Holtz, Goodman & Chick, P.C.

(57) ABSTRACT

A trocar is provided having a needle unit. The needle unit has a paracentetic section, which is substantially pyramidal. The paracentetic section has two curved surfaces that diagonally oppose each other. The surfaces are formed by cutting the ridges of the section, which diagonally oppose each other. The remaining two ridges of the paracentetic section make, respectively, sharp cutting edges for cutting living tissues. The cutting edges are substantially symmetrical to each other with respect to the axis of the needle unit.

22 Claims, 10 Drawing Sheets

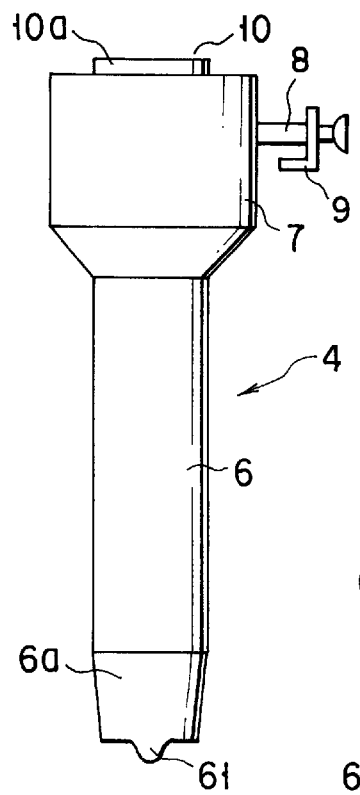 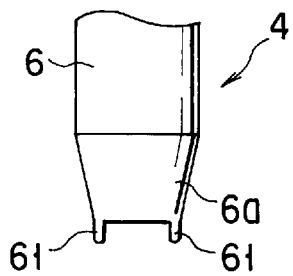 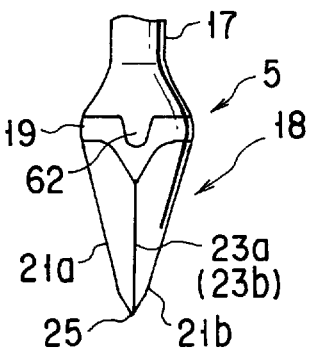
FIG. 8A  FIG. 8B  FIG. 8C
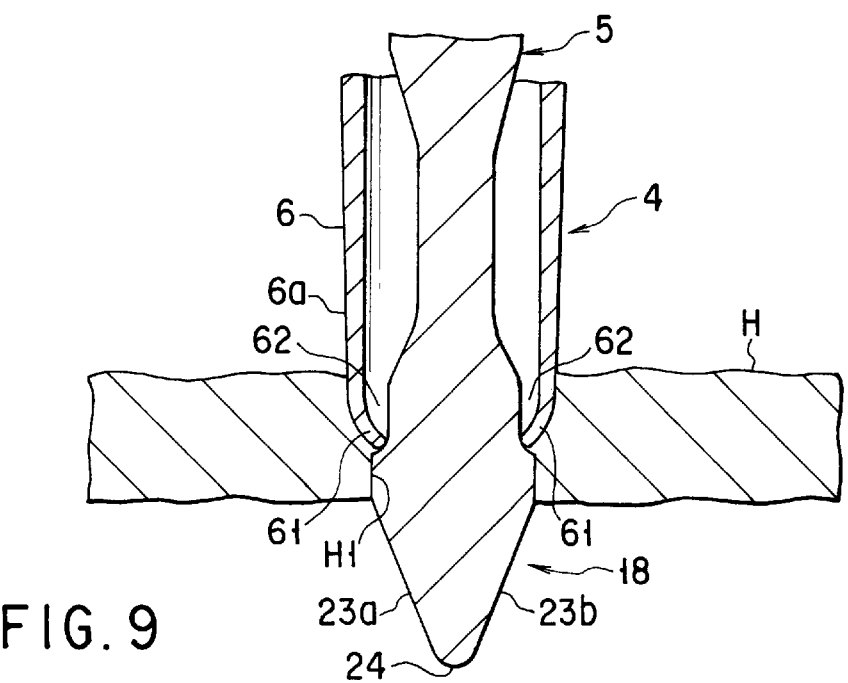
FIG. 9

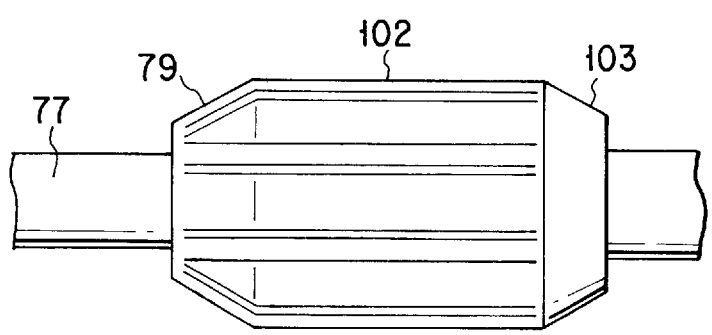
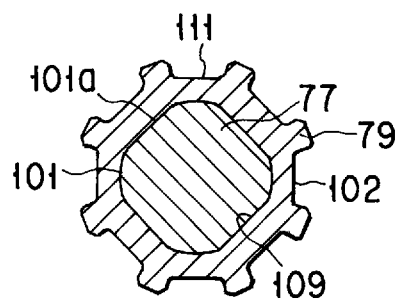
FIG. 19A
FIG. 19C
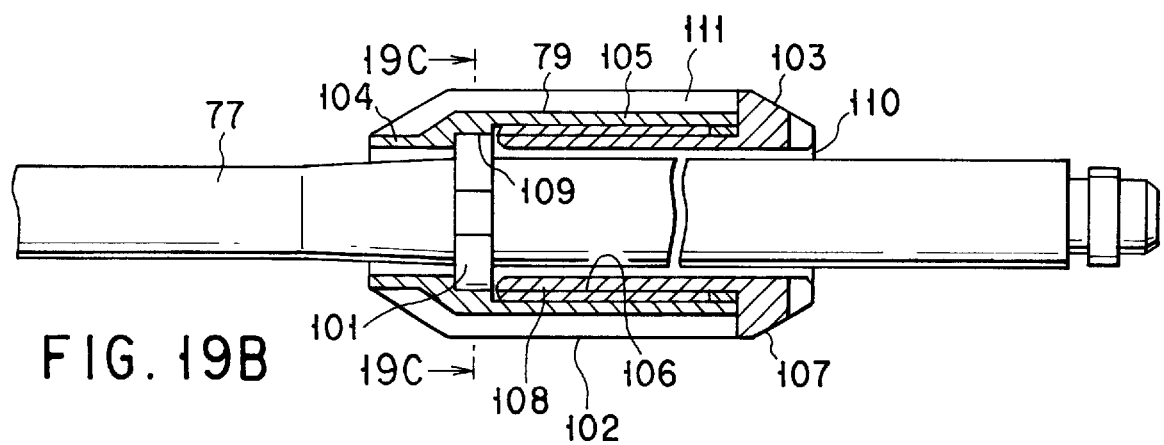
FIG. 19B
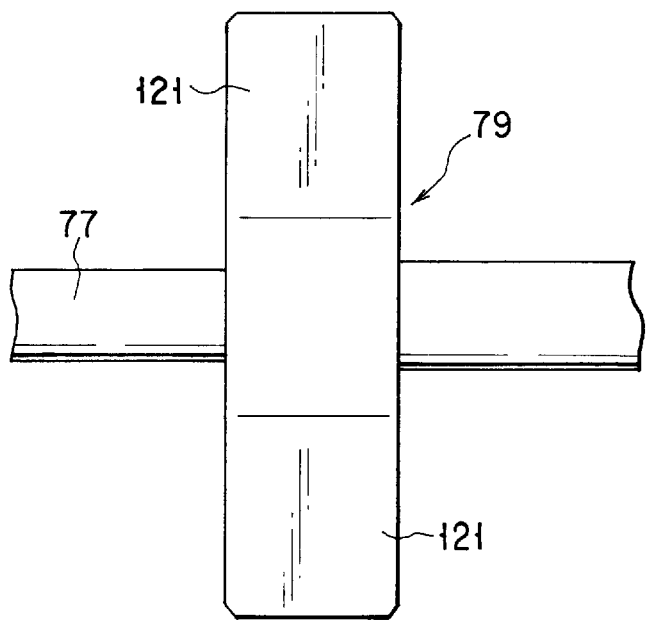
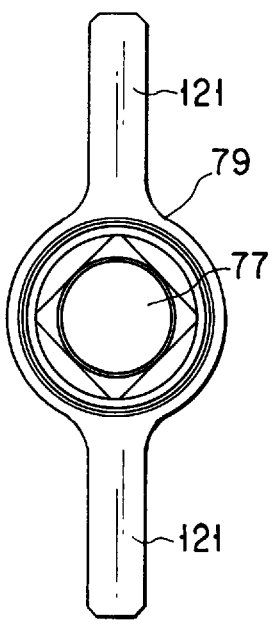
FIG. 20A
FIG. 20B

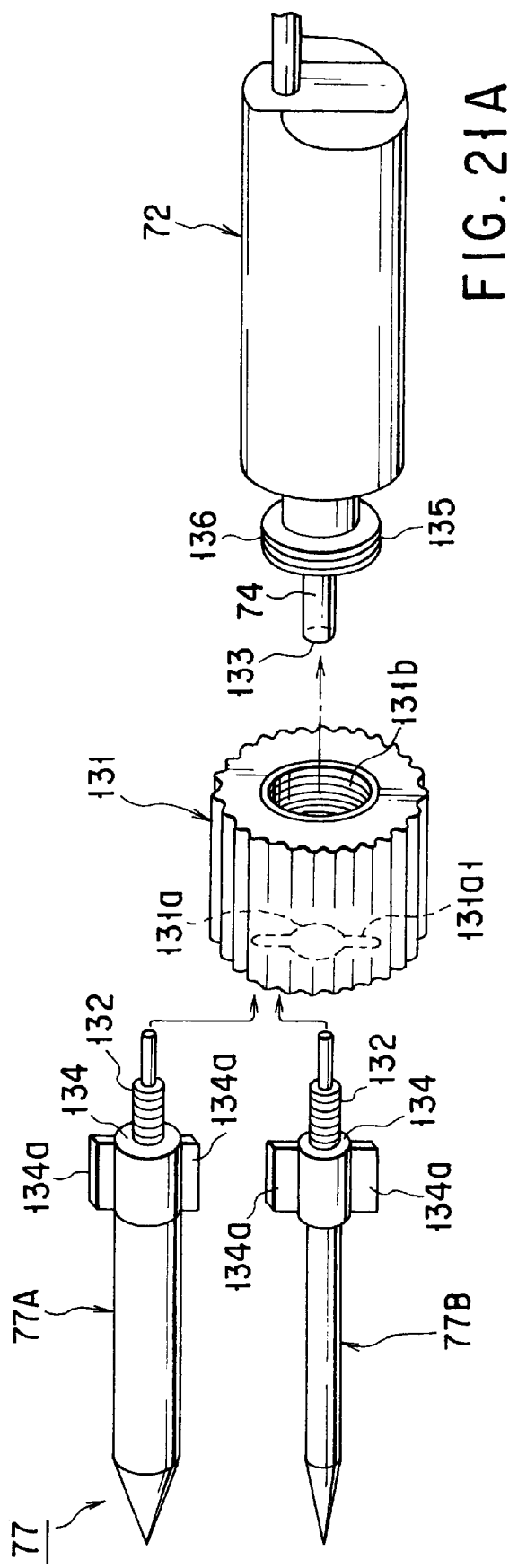

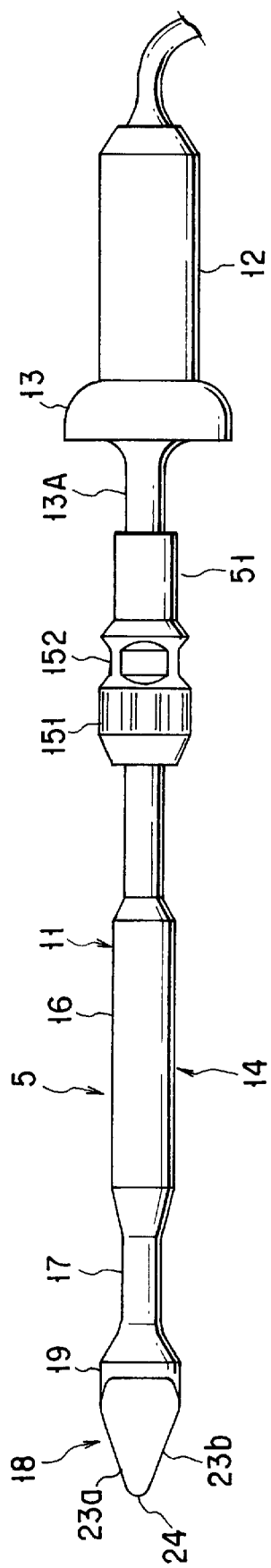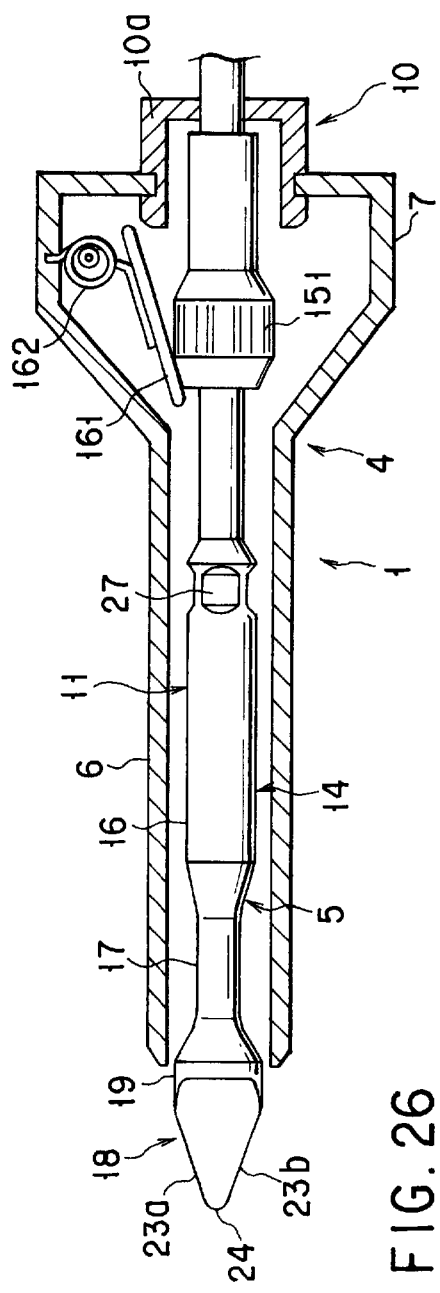
FIG. 25
FIG. 26

ULTRASONIC TROCAR

BACKGROUND OF THE INVENTION

The present invention relates to an ultrasonic trocar having a paracentetic section which is designed to penetrate the abdominal wall and to which ultrasonic vibration may be transmitted.

Disposable trocars are mainly used at present as devices that guide medical instrument into the abdominal cavity of a patient. U.S. Pat. No. 5,314,417 discloses a trocar of this type, which has a needle and a tubular sheath. The needle is pointed at its distal end and can penetrate the abdominal wall. The needle is inserted in the tubular sheath. The pointed distal end of the needle is a blade-shaped knife-edge. It is at the knife-edge that the needle penetrates the abdominal wall of the patient.

Most disposable trocars incorporate a safety shield mechanism. The mechanism works as a safety guard when the trocar is manipulated to pierce the abdominal wall with the needle. The mechanism has a safety shield. The safety shield contacts and covers the pierced part of the wall when the distal end of the needle penetrates into the abdominal cavity. Thus, the mechanism prevents the needle from further moving into the abdominal cavity, and thus preventing the tissues present in the abdominal cavity from being damaged.

Another type of a trocar is disclosed in U.S. Pat. 5,267,965. The needle of this trocar has a star-shaped distal end. It is at the star-shaped distal end that the needle penetrates the abdominal wall of the patient.

Reusable trocars are known. A reusable trocar is washed and sterilized after every use and is used again. Developed as reusable trocars are ultrasonic trocars, each having a paracentetic section to which ultrasonic vibration can be transmitted. The paracentetic section receives ultrasonic vibration during the use of the ultrasonic trocar. This enables the doctor to pass the paracentetic section through the abdominal wall with a relatively small force.

The paracentetic section of the needle of a typical ultrasonic trocar is shaped like a triangular pyramid. After every use of the ultrasonic trocar, the paracentetic section is sterilized with gas or heat so that the trocar may be used again.

The conventional trocars of the various types described above are disadvantageous in the following respects.

The disposable trocar has a safety shield that prevents the needle from further moving into the abdominal cavity. Having the safety shield, the disposable trocar is more complex in structure than otherwise. In other words, the disposable trocar has more parts, inevitably increasing the manufacturing cost. To make matters worse, the disposable trocar cannot be sterilized with gas or heat after it has been used once. It cannot be used again at all.

In the case of the disposable trocar disclosed in U.S. Pat. No. 5,314,417, the knife-edge becomes dull after use. Were the trocar used again, the doctor should apply a large force to pass the paracentetic section through the abdominal wall. Hence, the paracentetic section might move too deep into the abdominal cavity, possibly damaging the organs which exist in the abdominal cavity and which need not be treated at all.

In the case of conventional ultrasonic trocar, the paracentetic section, shaped like a triangular pyramid, makes a triangular incision hole in the abdominal wall. The incision hole is relatively large and possibly left open even after the ultrasonic trocar is removed from the abdominal wall. As a consequence, it may take a long time to heal the tissues in the abdominal wall. If the paracentetic section is a conical one, as the case may be, it will be more difficult for the doctor to pass this section through the abdominal wall than in the case where the section is shaped like a triangular pyramid. This is because the conical paracentetic section receives higher resistance while being passed through the abdominal wall than the triangular pyramidal one.

BRIEF SUMMARY OF THE INVENTION

The present invention has been made in consideration of the above. Its object is to provide an ultrasonic trocar that can be reusable, that can be manufactured at low cost, and that has a paracentetic section easy to pass through the abdominal wall, and that does not delay the healing of the tissues present in the abdominal wall.

To attain the object, the present invention provides an ultrasonic trocar, which has a tubular sheath and a needle unit inserted in the tubular sheath and designed to penetrate the abdominal wall while vibrated with ultrasonic waves. The ultrasonic trocar is characterized in that the needle unit has a substantially pyramidal paracentetic section at a distal end, and the paracentetic section has two cutting surfaces formed by cutting diagonally opposing two ridges, and two sharp cutting edges for cutting living tissues. The sharp cutting edges are provided at the two other diagonally opposing ridges and positioned symmetrically with respect to an axis of the needle unit.

To set the tubular sheath in an incision made in the abdominal wall, ultrasonic vibration is transmitted to the needle unit. The paracentetic section of the needle unit, which is vibrating, is brought into contact with the abdominal wall. At least the cutting edges at the distal portion of the two opposing ridges of the paracentetic section cut the abdominal wall easily, making an incision in the abdominal wall and the peritoneum. As the paracentetic section of the needle unit is inserted into the incision, the cutting edges of the paracentetic section gradually cut the abdominal wall. As a result, the paracentetic section is inserted into the abdominal cavity. The paracentetic section, which is the thickest part of the needle unit, receives a larger force than any other part of needle unit. Hence, the cutting edges, which constitute the thickest part of the unit, cut the abdominal wall efficiently. The distal end portion of the insertion section of the tubular sheath can therefore be smoothly inserted into the incision made in the abdominal wall. In the process of incising the abdominal wall, the curved surfaces of the paracentetic section do not damage the tissues existing in the abdominal wall. This helps to heal the tissue in the abdominal wall within a relatively short time.

The distal end part of the needle unit has curved surfaces and two ridges. The ridges are symmetrical with respect to the axis of the needle unit, each defined by at least two curved surfaces. Edges for cutting living tissues are provided at the distal parts of the ridges and at the proximal, or thickest parts of the ridges. Thus, the present invention can provide an ultrasonic trocar which can used again and again, helping to decrease medical cost, which can be smoothly inserted into the incision made in the abdominal wall and which does not damage the tissues in the abdominal wall.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 8A is a side view of the tubular sheath of the ultrasonic trocar according to the sixth embodiment of the invention;

FIG. 8B is a side view of the distal end of the tubular sheath shown in FIG. 8A;

FIG. 8C is a side view of the paracentetic section of the needle;

FIG. 9 is a longitudinal sectional view showing the tubular sheath shown in FIG. FIG. 8A and the needle unit partly inserted in the tubular sheath;

FIG. 19A is a side view of the probe of an ultrasonic medical device according to the fourteenth embodiment, showing the main section of the probe;

FIG. 19B is a longitudinal sectional view of the probe illustrated in FIG. 19A;

FIG. 19C is a sectional view, taken along line 19C—19C in FIG. 19B;

FIG. 20A is a side view of the torque-generating section of the probe of an ultrasonic medical device according to the fifteenth embodiment of the present invention;

FIG. 20B is a front view of the torque-generating section shown in FIG. 20A;

FIG. 21A is an exploded view of an ultrasonic medical device, which is the sixteenth embodiment of the invention;

FIG. 21B is a front view of one end of a rotary ring shown in FIG. 21A;

FIG. 21C is a partly sectional side view of the rotary ring shown in FIG. 21A;

FIG. 21D is a front view of the other end of the rotary ring shown in FIG. 21A;

FIG. 25 is a side view of the needle unit of an ultrasonic trocar, which is the nineteenth embodiment of the invention; and FIG. 26 is a longitudinal sectional view of an ultrasonic trocar according to the twentieth embodiment of the invention, showing the tubular sheath and the needle unit partly inserted in the tubular sheath.

DETAILED DESCRIPTION OF THE INVENTION

Figures 1A, 1B:
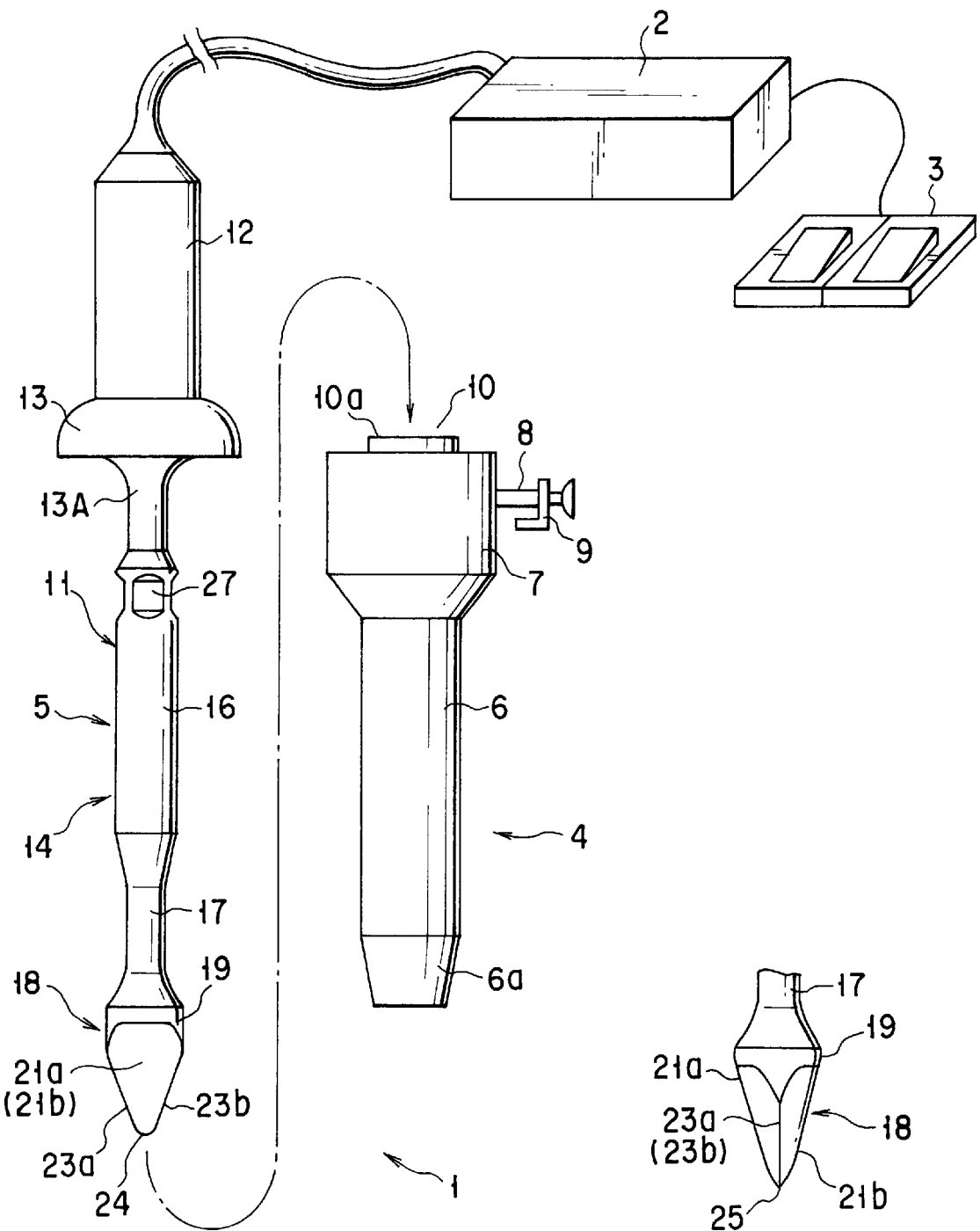
FIG. 1A is a partly perspective view of the ultrasonic trocar system according to the first embodiment of the invention.
FIG. 1B is a plan view of the paracentetic section that the needle of the ultrasonic trocar shown in FIG. 1A.

The first embodiment of the present invention will be described with reference to FIGS. 1A and 1B, FIG. 2 and FIGS. 3A to 3D. FIG. 1A shows the ultrasonic trocar system according to the first embodiment. The system comprises an ultrasonic trocar 1, an ultrasonic oscillation device 2, and a foot switch 3. The ultrasonic oscillation device 2 is connected to the ultrasonic trocar 1. The foot switch 3 is connected to the ultrasonic oscillation device 2 to turn the oscillation device 2 on and off.

The ultrasonic trocar 1 comprises a tubular sheath 4 and a needle unit 5. The needle unit 5 is removably inserted in the tubular sheath 4. The tubular sheath 4 has a thin, long insertion section 6 and a grip section 7. The insertion section 6 will be set in an incision made in the body wall of the patient (e.g., the abdominal wall) during the use of the ultrasonic trocar 1. The grip section 7 is coupled to the proximal end of the insertion section 6. The section 6 is tapered at the circumferential surface 6a. The grip section 7 has a gas inlet cap 8 on the circumferential surface. Pneumoperitoneal gas is supplied into the tubular sheath 4 through the gas inlet cap 8, if necessary. A three-way valve 9 is provided on the gas inlet cap 8.

The grip section 7 has an opening made in the top. It is through this opening that the needle unit 5, the insertion sections of endoscopes, and various medical instruments may be inserted into a body cavity of the patient. An outer seal 10 is mounted on the top of the grip section 7. The outer seal 10 is a ring-shaped seal member 10a, which surrounds the opening made in the top of the grip section 7.

The seal member 10a has an inner diameter smaller than the outer diameter of the needle unit 5, the outer diameters of endoscopes and the outer diameters of the medical instruments. While the needle unit 5, an endoscope or a medical instrument is being forced into the tubular sheath 4 through the outer seal 10, the seal member 10a keeps closing the gap between the tubular sheath 4 and the needle unit 5, the endoscope or the medical instrument. This prevents the pneumoperitoneal gas from leaking from the abdominal cavity.

A valve (not shown), i.e., inner seal, is provided in the tubular sheath 4. The valve remains closed, no matter whether the unit 5, an endoscope or a medical instrument is inserted into the abdominal cavity or pulled therefrom.

The needle unit 5 comprises an elongated probe 11, a hand piece 12, and a knob 13. The hand piece 12 is connected to the proximal end of the probe 11. The knob 13 is provided on the distal end of the hand piece 12. The hand piece 12 incorporates an ultrasonic oscillation device (not shown) and has a horn 13A connected to the proximal end of the probe 11. The horn 13A is coaxial with the knob 13. The horn 13A has a screw hole (not shown) in the distal end.

Figure 2:
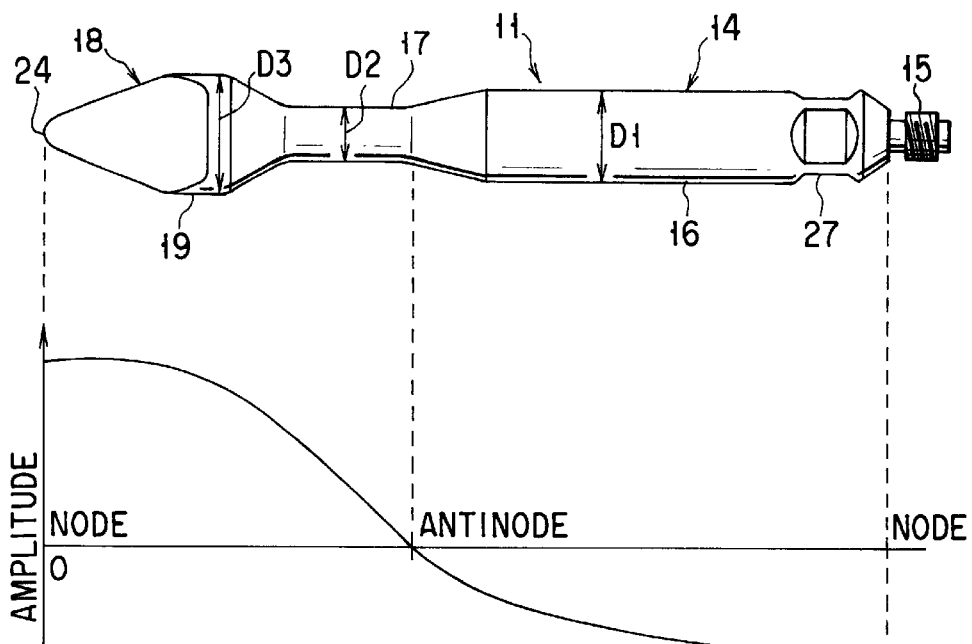
FIG. 2 is a diagram representing the vibration characteristic of the needle of the ultrasonic trocar shown in FIG. 1A.

The probe 11 has a rod-shaped probe body 14. As shown in FIG. 2, the probe body 14 has a male screw 15 at the proximal end. The male screw 15 is set in the screw hole of the horn 13A, whereby the probe 11 is fastened to the horn 13A.

The probe body 14 has a proximal section 16 and a middle section 17. The proximal section 16 has a diameter D1 and a predetermined length and is connected to and made integral with the distal end of the proximal section 16. The middle section 17 has a diameter D2 and a prescribed length and is connected to and made integral with the distal end of the middle section 17. A paracentetic section 18 is connected to and made integral with the distal end of the middle section 17. The paracentetic section 18 is shaped and has a predetermined length. The thickest part of the section 18 has a diameter D3. The diameter D2 of the middle section 17 is smaller than the diameter D1 of the proximal section 16, and the diameter D3 of the thickest part of the paracentetic section 18 is larger than the diameter D1 of the proximal section 16. Namely, D3>D1>D2.

As shown in FIG. 2, too, the proximal end of the proximal section 16 is located at the antinode of an ultrasonic wave that represents the ultrasonic vibration characteristic of the probe 11. The junction between the proximal section 16 and middle section 17 of the probe 11 is located at a node of the ultrasonic wave, and the distal end of the paracentetic section 18 of the probe 11 is located at the antinode of the ultrasonic wave, which precedes said node.

Figure 3A:
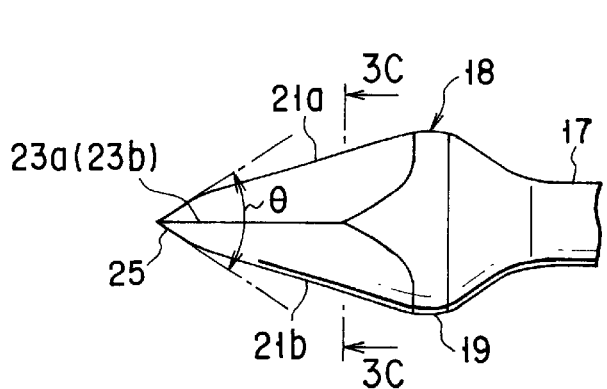
FIG. 3A is a plan view of the paracentetic section, showing the cutting edges of the paracentetic section.
Figure 3C:
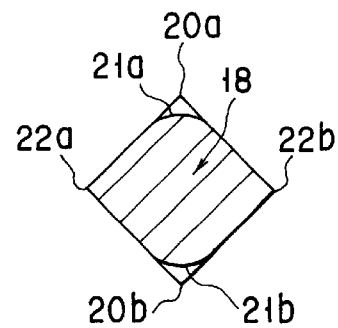
FIG. 3C is a sectional view of the paracentetic section, taken along line 3C—3C in FIG. 3A.

As illustrated in FIG. 3C, the paracentetic section 18, which is pyramidal, has two curved surfaces 21a and 21b that diagonally oppose each other. The surfaces 21a and 21b are formed by cutting the ridges 20a and 20b of the section 18, which diagonally oppose each other. The remaining two ridges 22a and 22b of the paracentetic section 18 make sharp cutting edges 23a and 23b, respectively.

Figure 3B:
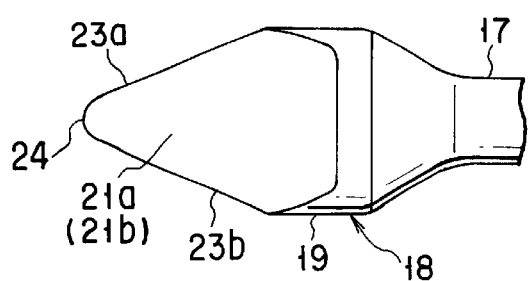
FIG. 3B is a side view of the paracentetic section of the needle.

As shown in FIG. 3B, a tip 24 of the paracentetic section 18 is rounded as viewed from above either curved surface (21a or 21b). The tip 24 has a radius R of curvature of, for example, about 3 mm or less.

FIG. 3A shows the paracentetic section 18 rotated around its axis by 90° from the position shown in FIG. 3B. As shown in FIG. 3A, a sharp tip 25 of the paracentetic section 18 is pointed as viewed from above either cutting edges (23a or 23b). The angle θ at which the tip 25 is pointed ranges, for example, from 45° to 90°.

Figure 3D:
FIG. 3D is a longitudinal sectional view, showing the layer coated on the paracentetic section of the needle.

As shown in FIG. 3D, the paracentetic section 18 is coated with a layer 26. The layer 26 is made of, for example, TiN, and is formed by means of TiN coating (PVD). Due to the layer 26, the paracentetic section 18 is resistant to wear, as a whole.

The probe 11 has two diametrically opposing flat surfaces 27, a little distal of the male screw 15. It is at these flat surfaces 27 that the probe 11 can be held with a spanner or the like, in the process of setting the male screw 15 in, or removing the male screw 15, the screw hole of the hand piece 12 or removing the male screw 15 from the screw hole.

The knob 13 of the needle unit 5 has a recess (not shown) in the distal end. The recess has the same shape as the outer seal 10 and is coaxial with the knob 13. When the needle unit 5 is inserted into the tubular sheath 4, it is set in the grip section 7 of the tubular sheath 4, with the outer seal 10 fitted in the recess made in the distal end of the grip section 13 of the needle unit 5. At this time, the paracentetic section 18 of the needle unit 5 protrudes from the distal end of the insertion section 6 of the tubular sheath 4.

How the ultrasonic trocar system is operated will be explained. To use the ultrasonic trocar 1, the needle unit 5 is inserted into the tubular sheath 4. The needle unit 5 is set in the tubular sheath 4, with the paracentetic section 18 protruding from the distal end of the insertion section 6 of the tubular sheath 4.

Thereafter, the foot switch 3 is operated, driving the ultrasonic oscillation device 2. The device 2 generates ultrasonic vibration, which is transmitted to the hand piece 12 of the ultrasonic trocar 1. The ultrasonic vibration is transmitted from the hand piece 12 to the probe 11 and further to the paracentetic section 18 of the needle unit 5. To use the ultrasonic trocar 1, a doctor manipulates the trocar 1 as will be described below.

First, the doctor holds, with the hand, grip section 7 of the tubular sheath 4, together with the grip section 13 of the needle unit 5. Next, he or she sets the paracentetic section 18 of the needle unit 5 in contact with the abdominal wall of the patient.

The doctor can easily make, in the abdominal wall and the peritoneum, an incision that extends into the abdominal cavity. This is because the sharp tip 25 of the paracentetic section 18, contacting the abdominal wall, is vibrating. The doctor inserts the ultrasonic trocar 1 into the incision. As the paracentetic section 18 of the needle unit 5 is inserted into the incision, the cutting edges 23a and 23b at the ridges 22a and 22b of the paracentetic section 18 gradually cut the abdominal wall. As a result, the paracentetic section 18 is inserted into the abdominal cavity.

In the process of pushing the ultrasonic trocar 1 into the abdominal cavity, the paracentetic section 18, which is the thickest part of the needle unit 5, receives a larger force than any other part of needle unit 5. Hence, the cutting edges 23a and 23b, which constitute the thickest part of the unit 5, cut the abdominal wall efficiently. The doctor only needs to move the trocar 1 toward the abdominal cavity with a small force. The distal end portion of the insertion section 6 of the tubular sheath 4 can therefore be smoothly inserted into the incision made in the abdominal wall.

In the process of pushing the ultrasonic trocar 1 onto the abdominal cavity to incise the same, the curved surfaces 21a and 21b of the paracentetic section 18 do not damage the tissues existing in the abdominal wall. As described above, the curved surfaces 21a and 21b diagonally oppose each other. Hence, after the ultrasonic trocar 1 is pulled out of the abdominal cavity, the incision closes, forming a scar, which is substantially straight and linear.

The ultrasonic trocar 1 is advantageous in the following respects.

As mentioned above, the paracentetic section 18, i.e., the distal end portion of the probe 11 of the needle unit 5, is shaped pyramidal. The section 18 has two curved surfaces 21a and 21b formed by cutting the diagonally opposing two ridges 20a and 20b and also has two cutting edges 23a and 23b. The cutting edges 23a and 23b are the two other diagonally opposing ridges 22a and 22b and designed to cut living tissues. Thus, when ultrasonic vibration is transmitted to the paracentetic section 18 set in contact with the abdominal wall, the cutting edges 23a and 23b easily cut the abdominal wall, making an incision in the abdominal wall and the peritoneum.

Further, the cutting edges 23a and 23b, which constitute the thickest part of the unit 5, can cut the abdominal wall efficiently. This is because the paracentetic section 18, i.e., the thickest part of the needle unit 5, receives a larger force than any other part of needle unit 5 while the ultrasonic trocar 1 is inserted into the abdominal cavity. Hence, the distal end portion of the tubular sheath 4 can be smoothly inserted into the incision made in the abdominal wall, along with the paracentetic section 18. The doctor only needs to move the trocar 1 toward the abdominal cavity with a small force. This reduces the paracentetic section 18 from being inserted deeper into the abdominal cavity than necessary and from damaging the organs present in the abdominal cavity.

The larger the diameter of the insertion section of the trocar 1, the less the force with which to insert the ultrasonic trocar 1 into the abdominal cavity. The experiments conducted by the inventors hereof showed that the force was particularly small when the paracentetic section 18 had a diameter ranging from 3 mm to 12 mm. Thus, the ultrasonic trocar 1 is advantageous, in safety, over the conventional reusable trocars and disposable trocars.

The ultrasonic trocar 1 does not have such a complex safety shield mechanism as the conventional disposable trocars. Therefore, the trocar 1 can be sterilized with gas or heat after every use. That is, the trocar 1 is reusable, helping to decrease medical cost.

The curved surfaces 21a and 21b of the paracentetic section 18 neither cut nor damage the tissues in the abdominal wall in the process of incising the abdominal wall. Since the surfaces 21a and 21b diagonally oppose each other, the incision closes, forming a scar, which is substantially straight and linear, after the ultrasonic trocar 1 is pulled out of the abdominal cavity. This serves to heal the tissues present in the abdominal wall within a relatively short time.

As shown in FIG. 3B, the tip 24 of the paracentetic section 18 is rounded as viewed from above either curved surface (21a or 21b). Nonetheless, the paracentetic section 18 can smoothly and reliably penetrate the peritoneum from the abdominal wall, because the rounded tip 24 has a radius R of curvature of about 3 mm or less. If the radius R exceeds 3 mm, it will be difficult for the section 18 to penetrate the peritoneum. In this case, cavitation may occur, separating the peritoneum from the abdominal wall.

Figure 4A:
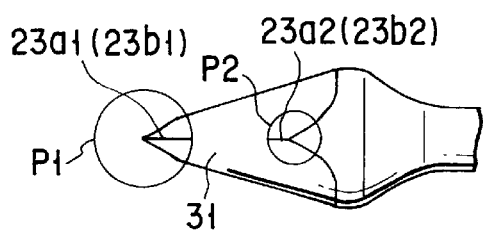
FIG. 4A is a plan view of the paracentetic section of the ultrasonic trocar according to the second embodiment, showing the cutting edges of the paracentetic section of the needle.
Figure 4B:
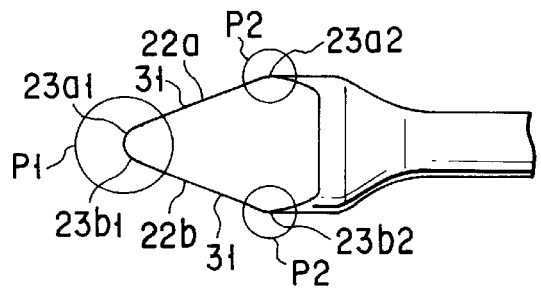
FIG. 4B is a side view of the paracentetic section shown in FIG. 4A.

FIGS. 4A and 4B show the paracentetic section of the needle unit of the ultrasonic trocar according to the second embodiment. The cutting edges of this paracentetic section are modification of the cutting edges 23a and 23b of the first embodiment.

More specifically, sharp edges 23a1 and 23a2 are formed at only the distal (thinnest) and proximal (thickest) parts of the ridge 22a of the paracentetic section 18, respectively. And two other sharp edges 23b1 and 23b2 are formed respectively at only the distal (thinnest) and proximal (thickest) parts of the other ridge 22b that diagonally opposes the ridge 22a. (Namely, the edges 23a1, 23a2, 23b1 and 23b2 are provided at only the parts of the ridges 22a and 22b, which are indicated by circles in FIGS. 4A and 4B.) The middle parts of the ridges 22a and 22b are cut, forming flat surfaces 31.

Since each of the ridges 22a and 22b has two cutting edges at the distal and proximal parts, respectively, and a flat surface at the middle part, the needle unit 5 is easier to manipulate. The ultrasonic trocar according to the second embodiment is more advantageous than the first embodiment.

The sharp edges 23a1 and 23b1 formed at the distal parts of the opposing ridges 22a and 22b of the paracentetic section 18 can make an incision in the abdominal wall and the peritoneum as easily as the cutting edges 23a and 23b of the first embodiment. Further, the sharp edges 23a2 and 23b2 formed at the proximal parts of the ridges 22a and 22b can cut the abdominal wall and the peritoneum as smoothly as the cutting edges 23a and 23b of the first embodiment, as the ultrasonic trocar 1 is pushed toward the abdominal cavity.

Figure 5:
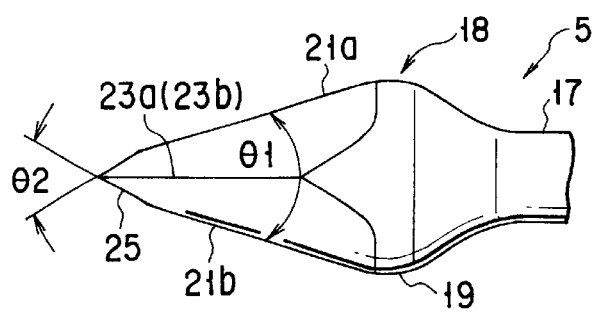
FIG. 5 is a plan view of the paracentetic section of the needle unit of the ultrasonic trocar according to the third embodiment, illustrating the cutting edges of the paracentetic section.

FIG. 5 shows the ultrasonic trocar according to the third embodiment of the invention. More precisely, it is a plan view of the paracentetic section 18 of the needle unit 5 of the ultrasonic trocar. This paracentetic section 18 is a modification of that of the first embodiment (FIGS. 1A and 1B, FIG. 2, and FIGS. 3A to 3D), as will be described below.

In the third embodiment, the pyramidal paracentetic section 18 is shaped such that the apex angle $\theta 1$ is smaller than the tip angle $\theta 2$ ($\theta 2 > \theta 1$) and that the tip angle $\theta 2$ ranges from 45° to 90° (45°$\leq \theta \leq$90°). The tip angle $\theta 2$ is the one that the section 18 has as viewed from above either cutting edge (23a or 23b).

Since the apex angle $\theta 1$ is smaller than the tip angle $\theta 2$ ($\theta 2 > \theta 1$), the paracentetic section 18 is relatively short. This decreases the possibility that the distal end portion of the section 18 that has penetrated the abdominal wall may damage the organs present in the abdominal cavity. Moreover, since the tip angle $\theta 2$ ranges from 45° to 90° (45°$\leq \theta 2 \leq$90°), the tip of the paracentetic section 18 need not be machined further. In other words, the section 18 can be machined with ease and efficiency.

Figure 6:
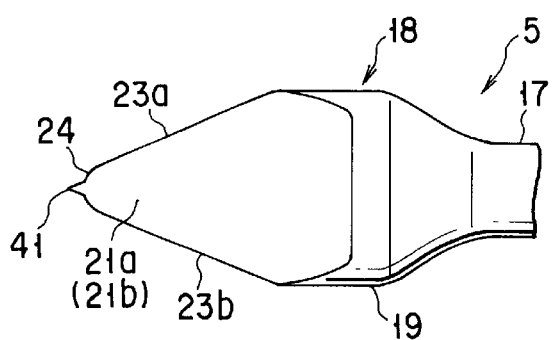
FIG. 6 is a plan view of the paracentetic section of the needle unit of the ultrasonic trocar according to the fourth embodiment.

FIG. 6 shows the paracentetic section of the needle unit of the ultrasonic trocar according to the fourth embodiment. The paracentetic section 18 of the fourth embodiment is a modification of the paracentetic section of the first embodiment (FIGS. 1A and 1B, FIG. 2, and FIGS. 3A to 3D), as will be described below.

As shown in FIG. 6, the section 18 has a small, needle-shaped projection 41 protruding from the apex. The projection 41 is sharp, making it easy to incise the abdominal wall when the ultrasonic trocar 1 is pushed onto the abdominal wall. As a result, the paracentetic section 18 can easily and smoothly penetrate the peritoneum from the abdominal wall. Thus, the peritoneum would not be separated from the abdominal wall as in the case of cavitation.

The fourth embodiment is an ultrasonic trocar 1, like the first to third embodiments. Nonetheless, it may be used as a trocar in which no ultrasonic vibration is transmitted to the paracentetic section. In this case, too, the needle-shaped projection 41 serves to accomplish reliable incision of the abdominal wall when the trocar is pushed onto the abdominal wall.

Figure 7:
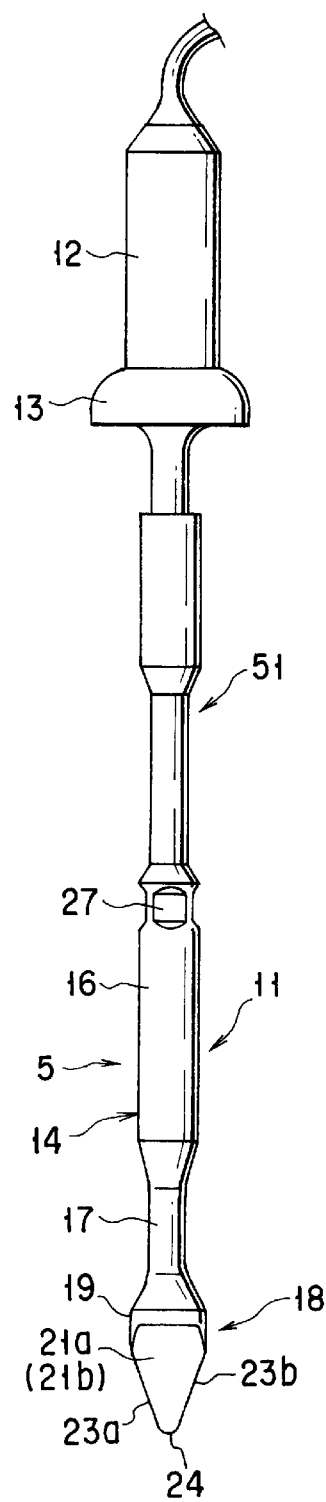
FIG. 7 is a side view of the paracentetic section of the needle unit of the ultrasonic trocar according to the fifth embodiment.

FIG. 7 is a side view of the paracentetic section of the needle unit of the ultrasonic trocar according to the fifth embodiment. The needle unit 5 of the fifth embodiment is a modification of that of the first embodiment (FIGS. 1A and 1B, FIG. 2, and FIGS. 3A to 3D), as will be described below.

As illustrated in FIG. 7, the probe 11 and the grip section 13 are connected together by a connection probe 51. The connection probe 51 has an appropriate length, adjusting the length of the needle unit 5. During the use of the ultrasonic trocar 1, the connection probe 51 amplifies the ultrasonic vibration transmitted to the paracentetic section 18. The section 18 is therefore vibrated vigorously. This reduces the force that the doctor needs to apply to pass the trocar through the abdominal wall. The ultrasonic trocar 1 can be inserted into the abdominal cavity more smoothly than otherwise.

FIGS. 8A to 8C and FIG. 9 show an ultrasonic trocar according to the sixth embodiment. More correctly, FIGS. 8A and 8B show the tubular sheath 4 of the trocar, FIG. 8C shows the paracentetic section 18 of the needle unit 5, and FIG. 9 shows the tubular sheath 4 and the needle unit 5 partly inserted in the sheath 4. The sixth embodiment is a modification of the first embodiment (FIGS. 1A and 1B, FIG. 2, and FIGS. 3A to 3D), as will be described below.

As shown in FIGS. 8A and 8B, two projections 61 extend from the distal end of the insertion section 6 of the tubular sheath 4. (The section 6 is tapered at the circumferential surface 6a.) Further, the paracentetic section 18 of the needle unit 5 has two engagement grooves 62 cut in the thickest part, as is illustrated in FIG. 8C. The projections 61 will fit into the grooves 62 when the needle unit 5 is inserted into the tubular sheath 4.

How the ultrasonic trocar according to the sixth embodiment is used will be explained.

First, the needle unit 5 is inserted into the tubular sheath 4. The ultrasonic trocar 1, i.e., a combination of the sheath 4 and the unit 5, is pushed onto the abdominal wall H. The paracentetic section 18 of the needle unit 5 penetrates the abdominal wall H, making an incision hole H1 in the abdominal wall H. As the distal end of the insertion section 6 of the tubular sheath 4 enters the incision hole H1, a force is applied from the inner surface of the hole H1 to both projections 61 that extend from the distal end of the section 6. The projections 61 are resiliently bent inwards, fitting into the engagement grooves 62 cut in the thickest part of the paracentetic section 18 as shown in FIG. 9. Hence, no stepped part exists between the tubular sheath 4 and the needle unit 5, and the junction between the sheath 4 and the unit 5 therefore smoothly passes the rim of the incision hole H1. Hence, the ultrasonic trocar 1 can be easily and smoothly inserted in the abdominal wall H.

The projections 61 may be permanently bent inwards. In this case, the projections 61 fit into the grooves 62 when the needle unit 5 is inserted into the tubular sheath 4, thus assembling the ultrasonic trocar 1. The trocar 1, thus assembled, can be inserted in the abdominal wall H more smoothly than in the case where the projections 61 are resiliently bent inwards as the distal end of the insertion section 6 of the sheath 4 enters the incision hole H1.

Further, the insertion section 6 of the tubular sheath 4 may have only one projection, three projections or more projections, instead of two projections 61, and the paracentetic section 18 may have only one groove, three grooves or more grooves, instead of two grooves 62.

The sixth embodiment is an ultrasonic trocar 1. Nonetheless, it may be used as a trocar in which no ultrasonic vibration is transmitted to the paracentetic section.

An ultrasonic medical device 71, which is the seventh embodiment of the present invention, will be described with reference to FIGS. 10 and 11.

Figure 10:
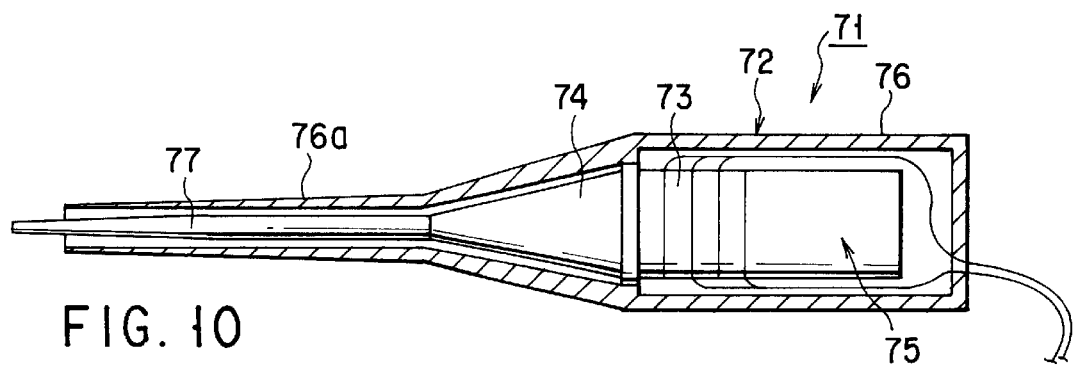
FIG. 10 is a longitudinal sectional view of an ultrasonic medical device according to the seventh embodiment of the invention.

As shown in FIG. 10, the ultrasonic medical device 71 has a hand piece 72. The hand piece 72 is electrically connected to the ultrasonic oscillation device 2 shown in FIG. 2. The hand piece 72 incorporates a vibration unit 75 that comprises an ultrasonic oscillator 73 and a horn 74. The ultrasonic oscillator 73 is a means for generating ultrasonic waves, such as a bolted Langevin type oscillator. The horn 74 is coupled with the ultrasonic oscillator 73 and amplifies the ultrasonic waves the oscillator 73 has generated. A cover 76 is removably mounted on the vibration unit 75, forming a grip section. The ultrasonic oscillator 73 has a plurality of elements that are laid one upon another. These elements may be either electrostrictive ones or magnetostrictive ones.

A probe 77 (vibration-transmitting member) is connected to the distal end of the vibration unit 75 incorporated in the hand piece 72. The probe 77 is made of metal such as titanium alloy or duralumin. As shown in FIG. 11, the probe 77 has male screw 78 at the proximal end. The male screw 78 is set in engagement with the female screw (not shown) provided in the distal end of the horn 74. Thus, the probe 77 is removably coupled, at its proximal end, to the distal end of the horn 74. The probe 77 may be coupled to the horn 74 by any means other than screw engagement, provided that it can be removably connected to the horn 74 when rotated.

A tubular sheath 76a covers the probe 77. The tubular sheath 76a is made integral with the cover 76. An annular space is provided between the outer circumferential surface of the horn 74 and the circumferential surface of the probe 77, on the one hand, and the inner circumferential surface of the tubular sheath 76a, on the other hand. The annular space may be used as a passage for guiding cooling fluid to the distal end of the sheath 76a.

In the ultrasonic medical device 71, the ultrasonic oscillator 73 is driven with the power supplied from the ultrasonic oscillation device 2. Thus driven, the ultrasonic oscillator 73 generates ultrasonic waves. The horn 74 amplifies the ultrasonic waves. The waves amplified are transmitted to the probe 77. The distal end portion of the probe 77 is thereby vibrated.

Figure 11:
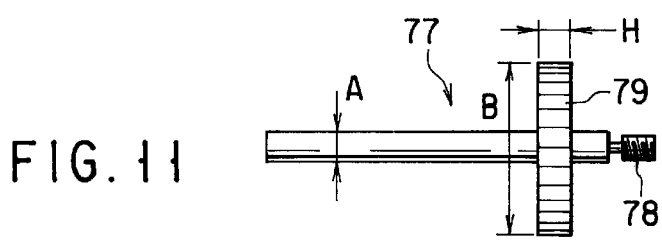
FIG. 11 is a side view of the probe of the ultrasonic medical device shown in FIG. 10.

FIG. 11 shows the probe 77 removed from the hand piece 72. The probe 77 is a solid, rod-shaped member. The distal end portion of the probe 77 forms a cutting edge, like the distal end portion of the paracentetic section 18 of the needle unit 5.

A torque-generating section 79 (not shown in FIG. 10), which is an annular member, is mounted on the probe 77 and located near the male screw 78. The torque-generating section 79 is made of plastic, such as PEEK (Polyetherethyle-ketone), PTFE (Teflon) or PSF (Polysulfone). The surface of the section 79 is knurled, having projections and depressions. The torque-generating section 79 is removably and rotatably connected to the probe 77.

The torque-generating section 79 can be held with fingers and rotated around the probe 77. When the section 79 is rotated so, it imparts a torque large enough to secure the probe 77 to, and remove the probe from, the horn 74. The ratio of the outer diameter B of the section 79 to the diameter of the probe 77, i.e., B/A (A<B), the width H of the section 79, and the position at which the section 97 is secured to the probe 77 are set such that the medical device 71 can serve to perform an ultrasonic treatment. (That is, the ratio B/A, the width H and the position do not reduce the efficiency of generating ultrasonic waves.)

Preferably, the ratio B/A is less than 3 (B/A<3). This relation does not depends on the oscillation frequency of the ultrasonic oscillator 73. If the ratio B/A is equal to or greater than 3, various problems (e.g., changes in impedance) during the transmission of ultrasonic waves. It has been found out that the probe 77 cannot be vibrated at all or will stop vibrating while the oscillator 73 is operating, if the ratio B/A is equal to or greater than 3.

The position, at which the torque-generating section 79 is secured to the probe 77, is important. If the section 79 takes a position near the male screw 78 as shown in FIG. 11, the section 79 will effectively apply a torque to the probe 77, facilitating the screw-engagement of the probe 77 with the distal end of the horn 74. In this case, however, the torque-generating section 79 is located at an antinode of the ultrasonic wave. Nonetheless, the section 79 can be driven, along with the probe 77, if the ultrasonic oscillator 73 has an oscillation frequency of 23.5 Hz, the width H is 10 mm or less and the ratio B/A is less than 3. This prevent the amplitude of ultrasonic vibration of the probe 77 from decreasing. If the amplitude of ultrasonic vibration of the probe 77 is large, the torque-generating section 79 may be located at a node of the ultrasonic wave.

The torque-generating section 79 may be removably fastened to the probe 77, by means of either screw engagement or elastic snapping. Alternatively, the section 79 can be permanently secured to the probe 77.

The use of the torque-generating section 79 results in the following advantages.

First, the torque-generating section 79 is large enough to impart a torque to the probe 77 when held with fingers and rotated. The probe 77 can therefore be easily fastened to, and separated from, the horn 74, when rotated with fingers. Any tool whatever, such as a spanner, need not be used to fasten the section 79 to the probe 77, or to remove the section 79 from the probe 77. This makes it possible to replace the probe 77 with another within a short time.

Secondly, the torque-generating section 79 need not be removed from the probe 77 during the use of the ultrasonic oscillation device 2. This is because section 79 does not obstruct the ultrasonic wave treatment performed by the use of the ultrasonic oscillation device 2. Since the section 79 can remain attached to the probe 77 during the use of the device 2, there is no need to worry about losing of the torque-generating section 79.

Thirdly, the doctor can perceive how firmly or loosely the probe 77 is fastened to the horn 74, by applying a force to rotate the section 79, more easily and accurately than in the case where the probe 77 is fastened to the horn 74 with a spanner or the like.

Figure 12A:
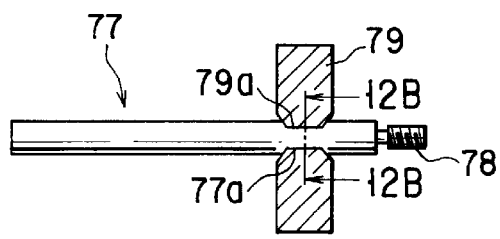
FIG. 12A is a longitudinal sectional view of the probe of an ultrasonic medical device according to the eighth embodiment of the invention.
Figure 12B:
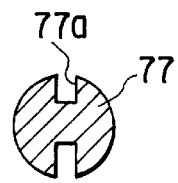
FIG. 12B is a sectional view, taken along line 12B—12B in FIG. 12A.

FIGS. 12A and 12B illustrate the probe of an ultrasonic medical device according to the eighth embodiment of the invention. In the eighth embodiment, the torque-generating section 79 is secured to the probe 77, unable to rotate with respect thereto. As shown in FIGS. 12A and 12B, the probe 77 has two grooves 77a in the circumferential surface and the section 79 has two projections 79a on the inner circumferential surface. The section 79 is mounted on the probe 77, with the projections 79a fitted in the grooves 77a. Therefore, the torque-generating section 79 cannot rotate at all with respect to the probe 77.

Figure 13A:
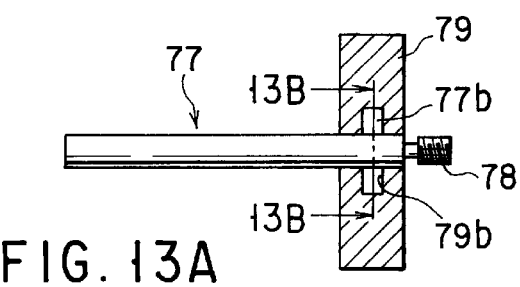
FIG. 13A is a longitudinal sectional view of the probe of an ultrasonic medical device according to the ninth embodiment of this invention.
Figure 13B:
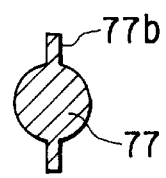
FIG. 13B is a sectional view, taken along line 13B—13B in FIG. 13A.

FIGS. 13A and 13B show the probe of an ultrasonic medical device according to the ninth embodiment of this invention. As shown in FIGS. 13A and 13B, the probe 77 has two projections 77b on the circumferential surface and the torque-generating section 79 has two holes 79b in the inner circumferential surface. The section 79 is mounted on the probe 77, with the projections 77b fitted in the holes 79b. Thus, the torque-generating section 79 cannot rotate at all with respect to the probe 77.

Figure 14A:
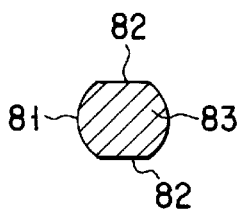
FIG. 14A is a cross sectional view of the first modification of the probe of the seventh embodiment of the invention.
Figure 14B:
FIG. 14B is a cross sectional view of the second modification of the probe of the seventh embodiment of the invention.
Figure 14C:
FIG. 14C is a cross sectional view of the third modification of the probe of the seventh embodiment of the invention.

FIGS. 14A to 14C show three modifications of the probe 77 of the seventh embodiment (FIGS. 10 and 11), each designed to prevent the torque-generating section 79 from rotating with respect to the probe 77.

The first modification of the probe 77, shown in FIG. 14A, has a part having an oblate cross section. The first modified probe has a portion 83 having a cross section of a special shape, for holding the torque-generating section 79. The portion 83 has been made by cutting a part of a round bar 81, forming two opposing flat surfaces 82 that are parallel to each other. The torque-generating section 79 is mounted on that part of the round bar 81.

The second modification of the probe 77, shown in FIG. 14B, has a part 84 having a square cross section. The second modified probe has been made by cutting a part of a round bar, forming four flat surfaces. The torque-generating section 79 is mounted on that part of the round bar.

The third modification of the probe 77, shown in FIG. 14C, has a part 85 having a rectangular cross section. The third modified probe has been made by cutting a part of a round bar, forming four flat surfaces. The torque-generating section 79 is mounted on that part of the round bar.

If the first modified probe shown in FIG. 14A is used, the torque-generating section 79 has an oblate hole and mounted on that part of the first modified probe which has an oblate cross section. If the second modified probe shown in FIG. 14B is used, the torque-generating section 79 has a square hole and mounted on that part of the second modified probe which has a square cross section. If the third modified probe shown in FIG. 14C is used, the torque-generating section 79 has a rectangular hole and mounted on that part of the third modified probe which has a rectangular cross section.

Figure 15:
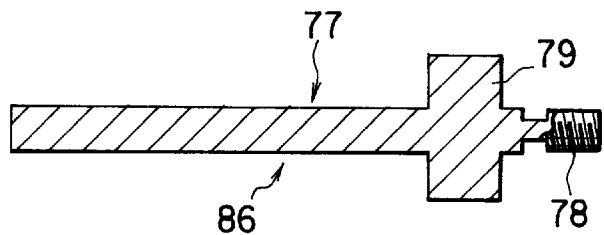
FIG. 15 is a longitudinal sectional view of the probe of an ultrasonic medical device according to the tenth embodiment of the invention.

FIG. 15 illustrates the probe of an ultrasonic medical device according to the tenth embodiment of the invention. The tenth embodiment is characterized in that a rod 77 and a torque-generating section 79 are combined, forming a probe 86.

Figure 16:
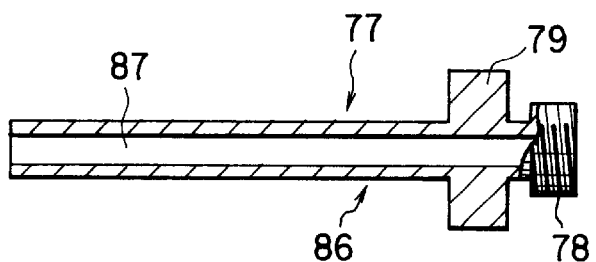
FIG. 16 is a longitudinal sectional view of the probe of an ultrasonic medical device according to the eleventh embodiment of this invention.

FIG. 16 shows the probe of an ultrasonic medical device according to the eleventh embodiment of this invention. The eleventh embodiment is characterized in that the probe 86, which is similar to the probe of the tenth embodiment (FIG. 15), has an axial though hole 87. That is, the probe 86 is a hollow member. The ultrasonic oscillator 73 and the horn 74 are also hollow members and are connected to a suction means. This enables the ultrasonic medical device to draw fluids from any tissue or organ that is being treated by the use of the device.

The structure of the seventh embodiment (FIGS. 10 and 11) can be applied to the ultrasonic trocars 1 according to the first embodiment (FIGS. 1A and 1B, FIG. 2, FIGS. 3A to 3D) to the sixth embodiment (FIGS. 8A and 8B). If so, the probe 77 of the ultrasonic medical device 71 will function as the needle unit 5 of the trocar 1, with its proximal end removably connected to the horn 74 incorporated in the hand piece 72. The ultrasonic vibration will be transmitted from the ultrasonic oscillator 73 to the distal end of the probe 77 through the horn 74.

An medical instrument can be inserted into the abdominal cavity through the trocar 1, in the following process.

At first, a pneumoperitoneal stylus is forced into the abdominal cavity through the abdominal wall. Gas is introduced into the cavity through the pneumoperitoneal stylus, thereby expanding the abdominal cavity so that medical instrument may be moved in the cavity easily.

Thereafter, the pneumoperitoneal stylus is pulled out of the abdominal cavity. The probe 77 is inserted into the guide hole of the tubular sheath 4 of the trocar 1. The probe 77 is vibrated with the ultrasonic waves supplied from the oscillator 73 via the horn 74. The probe 77 vibrating and functioning as a needle is pushed, at its distal end, onto the abdominal wall. The probe 77 makes an incision in the abdominal cavity and eventually pierces the abdominal wall, together with the tubular sheath 4. Thus, the ultrasonic trocar 1 is inserted into the expanded abdominal cavity through the incision made in the abdominal wall.

After the trocar 1 is set in the abdominal wall, extending into the abdominal cavity, the probe 77 is pulled from the abdominal cavity through the guide hole of the tubular sheath 4. A medical instrument is inserted into the abdominal cavity through the guide hole of the tubular sheath 4.

Having the probe 77 with a torque-generating section 79, the ultrasonic trocar 1 is advantageous in the following respects.

That is, the torque-generating section 79 of the probe 77, which is the needle of the trocar 1, can have a diameter greater, by 10 mm or more, than the probe for use in combination with an ordinary ultrasonic coagulation-incision device or the like. Hence, a large torque can be applied to the probe 77 by rotating the torque-generating section 79, without twisting the probe 77. This makes it easy to fasten the probe 77 to the horn 74 and separate the probe 77 therefrom.

Figure 17:
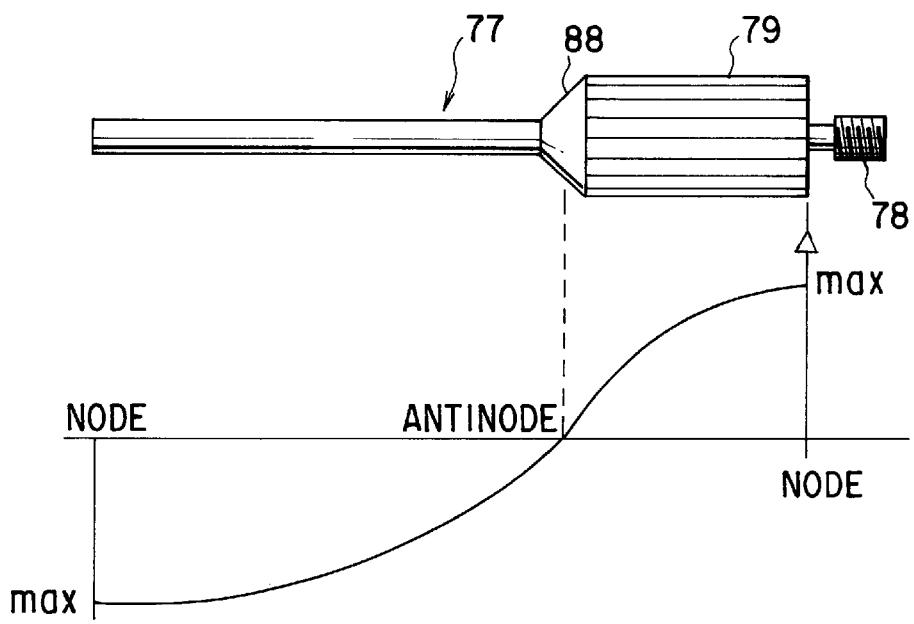
FIG. 17 is a longitudinal sectional view of the probe of an ultrasonic medical device according to the twelfth embodiment of the invention.

FIG. 17 shows the probe of an ultrasonic medical device according to the twelfth embodiment of the invention. The probe is the first modification of the probe of the seventh embodiment (FIGS. 10 and 11). This modified probe has a torque-generating section 79 that is long, extending forwards from an antinode to a node of the ultrasonic wave, for a quarter of the wavelength. In addition, the section 79 has a tapered end portion 88 at said node of the ultrasonic wave. The tapered end portion 88 can amplify the ultrasonic vibration, as may be well understood in the art. In other words, the torque-generating section 79 extends for a quarter of the wavelength from the antinode to the immediate node of the ultrasonic wave, and the probe 77 greatly decreases in diameter at this node. The ultrasonic vibration of the probe 77 can therefore be amplified.

Figure 18:
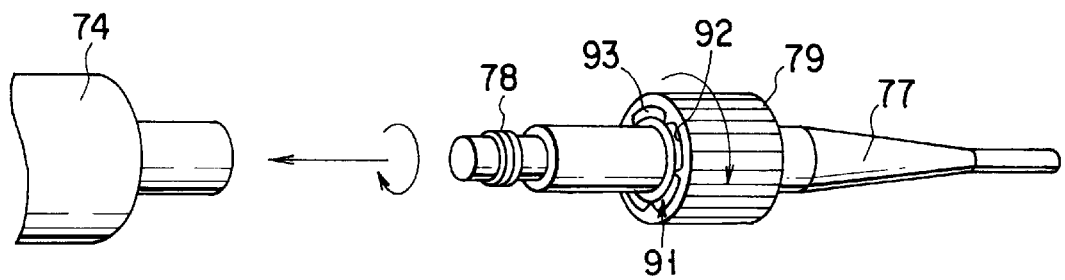
FIG. 18 is a longitudinal sectional view of the probe of an ultrasonic medical device according to the thirteenth embodiment of the invention.

FIG. 18 depicts the probe of an ultrasonic medical device according to the thirteenth embodiment of the invention. The probe is the second modification of the probe of the seventh embodiment (FIGS. 10 and 11). The second modified probe is characterized in that the torque-generating section 79 is mounted on the probe 77 and coupled thereto by a constant-force mechanism 91 so that the section 79 may function as a torque wrench.

More precisely, the inner circumferential surface of the section 79 is a ratchet surface 92 on which tooth are formed. Tooth 93 are formed on the circumferential surface of the probe 77 and can mesh with the tooth provided on the ratchet surface 93. The ratchet surface 92 and the tooth 93 constitute the constant-force mechanism 91. When the section 79 is rotated in the direction of the arrow (FIG. 18) to fasten the male screw 78 of the probe 77 to the horn 74, the tooth on the ratchet surface 92 93 of the probe 77 abut on the tooth 93 of the probe 77. A torque is thereby applied to the probe 77. When the torque applied to the probe 77 exceeds a predetermined value, the tooth on the ratchet surface 92 slip over the tooth 93 of the probe 77. That is, the constant-force mechanism 91 serves to fasten the probe 77 to the horn 74, preventing the probe 77 from rotated with an excessively large force.

Hence, the probe 77 is fastened to the horn 74, always with an optimal fastening force. As a result, the horn 74 can transmit the ultrasonic vibration to the probe 77 with stability and reliability. Since the probe 77 is fastened to the horn 74 with an appropriate force, it would not be coupled with the horn 74 so firmly that it is hardly disconnected from the horn 74.

It is desired that the torque-generating section 79 be attached to the probe 77 at a node of the ultrasonic wave. If the section 79 is so attached, the probe 77 will not vibrate at the node of the ultrasonic wave, and neither heat nor noise will be generated at the junction between the probe 77 and the section 79.

FIGS. 19A to 19C illustrate the probe of an ultrasonic medical device according to the fourteenth embodiment of the present invention. This probe is the third modification of the probe of the seventh embodiment (FIGS. 10 and 11). As shown in FIG. 19B, an annular flange 101 is mounted on that part of the probe 77 which is located at a node of the ultrasonic wave. The flange 101 serves to fasten the torque-generating section 79 to the probe 77. As shown in FIG. 19C, the flange 101 has four flat surfaces on the circumferential surface and, therefore, has a substantially square cross section.

The torque-generating section 79 comprises a pipe-shaped base member 102 and a pipe-shaped fastening member 103. The fastening member 103 is inserted in the base member 102 in screw engagement. The base member 102 consists of a small-diameter part 104 and a large-diameter part 105. The small-diameter part 104 has an inner diameter smaller than the inner diameter of the large-diameter part 105. The large-diameter part 105 has a screw hole 106.

The fastening member 103 has a ring-shaped head 107 at one end. A male screw 108 is cut in the outer circumferential surface of the fastening member 103, except the ring-shaped head 107. The male screw 108 is set in engagement with the screw hole 106 of the torque-generating section 79.

An annular groove 109 is made in the inner circumferential surface of the base member 102, at the bottom of the screw hole 106 of the torque-generating section 79. The annular groove 109 has a diameter larger than the inner diameter of the small-diameter part 104.

As shown in FIG. 19B, the flange 101 on the probe 77 is clamped between the torque-generating section 79 and the fastening member 103 set in screw engagement with the section 79. The section 79 is thereby fastened to the probe 77, at the node of the ultrasonic wave. The torque-generating section 79 is fastened to the flange 101, with a gap 110 provided between the outer circumferential surface of the probe 77 and the inner circumferential surface of the section 79.

As shown in FIG. 19C, a plurality of parallel, axial grooves 111 are cut in the outer circumferential surface of the base member 102 of the torque-generating section 79. These grooves 111 make it easy for the doctor to hold the torque-generating section 79.

The ultrasonic medical device, which is the fourteenth embodiment of the invention, is advantageous in the following respects.

Even if the probe 77 vibrate a little at the node of the ultrasonic wave, heat will hardly be generated at the interface between the probe 77 and the torque-generating section 79. This is because the gap 110 is provided between the outer circumferential surface of the probe 77 and the inner circumferential surface of the section 79. Heat, if any, generated at this interface will be scarcely transmitted to the section 79, also thanks to the gap 110.

The constant-force mechanism 91 used in the thirteenth embodiment (FIG. 18) may be employed in the fourteenth embodiment. If this is the case, the torque-generating section 79 may function as a torque wrench. Further, it is easy to rotate the torque-generating section 79, because the section 79 has a plurality of axial grooves 111 cut in the outer circumferential surface.

FIGS. 20A and 20B show the torque-generating section 79 of an ultrasonic medical device according to the fifteenth embodiment of the invention. This torque-generating section 79 is, so to speak, a modification of the section 79 of the seventh embodiment (FIGS. 10 and 11). The section 79 has two finger rests 121, which extend from the outer circumferential surface in the radial direction of the section 79. By virtue of the finger rests 121, the section 79 can generate a large torque when held with fingers and rotated around its axis.

FIGS. 21A to 21D show an ultrasonic medical device, which is the sixteenth embodiment of the present invention. The sixteenth embodiment is identical to the seventh embodiment (FIGS. 10 and 11), except for the mechanism for securing the probe 77 to, and separating the probe 77 from, the horn 74. The components similar or identical to those shown in FIGS. 10 and 11 are designated at the same reference numerals and will not described in detail.

In the sixteenth embodiment, the probe 77 can be secured to and removed from the hand piece 72 by means of a rotary ring 131. FIG. 21A shows two probes 77A and 77B which different in diameter. The first probe 77A has a diameter of, for example, 10 mm. The second probe 77B has a diameter of, for example, 5 mm. The probes 77A and 77B have each a male screw 132 at the proximal end. The male screws 132 of both probes 77A and 77B have the same diameter.

The horn 74 of the hand piece 72 has a screw hole 133 in its distal end portion. The probes 77A and 77B is interchangeably fastened to the horn 74, with the male screw 132 set in the screw hole 133 made in the distal end portion of the horn 74.

The rotary ring 131 has an engagement hole 131a in one end, and a screw hole 131b in the other end. As shown in FIG. 21C, an annular groove 131c is cut in the inner circumferential surface of the rotary ring 131 and located between the engagement hole 131a and the screw hole 131b. As shown in FIG. 21B, a pair of recesses 131a1 are made in the inner circumferential surface of rotary ring 131 and located at the engagement hole 131a. The recesses 131a1 extend in the opposite directions.

The probes 77A and 77B have each an engagement part 134 at the proximal end and near the male screw 132. The engagement part 134 of either probe can be set into the engagement hole 131a of the rotary ring 131. The part 134 has a pair of projections 134a, which protrude in the opposite directions from the circumferential surface of the engagement part 134. Once the engagement part 134 is set in the engagement hole 131a, extending through the hole 131a for a predetermined distance, the projections 134a fit into the recesses 131a1 that are made in the inner circumferential surface of rotary ring 131. The engagement parts 134 of the probes 77A and 77B, each having two projections 134a, are identical in shape and size.

A torque-generating section 135 is mounted on the horn 74 of the hand piece 72. The torque-generating section 135 has a male screw 136 on its circumferential surface. The male screw 136 can be set in the screw hole 131b of the rotary ring 131, to a predetermined depth from the proximal end of the rotary ring 131.

The annular groove 131c cut in the inner circumferential surface of the rotary ring 131 is a width greater than that of the torque-generating section 135. Thus, the section 135 can loosely fit in the annular groove 131c and can be rotated.

How the ultrasonic medical device according to the sixteenth embodiment is used will be explained.

First, the torque-generating section 135 of the horn 74 is set into the screw hole 131b of the rotary ring 131. Then, the rotary ring 131 is rotated until the section 135 reaches the annular groove 131c and rotatably fits into the annular groove 131c. The rotary ring 131 is thereby rotatably coupled to the horn 74. Thereafter, the engagement part 134 of the probe 77A or 77B is inserted into the engagement hole 131a of the rotary ring 131. The rotary ring 131 is rotated, rotating the probe 77A or 77B. As a result, the male screw 132 of the probe 77A or 77B is set into the screw hole 133 of the horn. Either the probe 77A or the probe 77B is thereby coupled to the horn 74.

The sixteenth embodiment is advantageous in that the probes 77A and 77B having different diameters can be easily secured to and removed from the hand piece 71, without the necessity of using a spanner. In the sixteenth embodiment it is desired that the rotary ring 131 be always secured to the horn 74, so as not to go astray.

Figure 22:
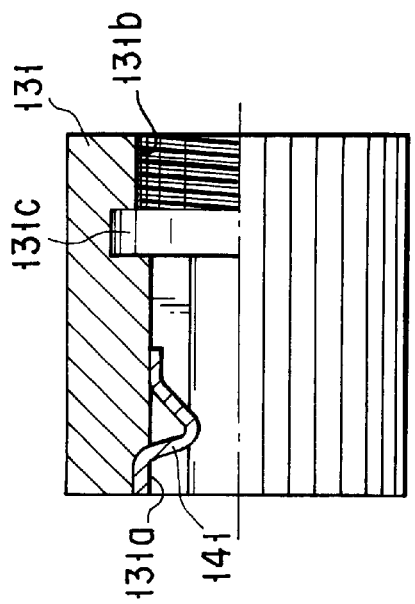
FIG. 22 is a partly sectional side view of the rotary ring of an ultrasonic medical device according to the seventeenth embodiment of the present invention.

FIG. 22 shows the rotary ring of an ultrasonic medical device according to the seventeenth embodiment of the invention. This device is a modification of the sixteenth embodiment (FIGS. 21A to 21C). As shown in FIG. 22, a leaf spring 141 is provided in the engagement hole 131a of the rotary ring 131. The leaf spring 141 pushes the projections 134a of the probe 77 toward the hand piece 72, which are inserted in the engagement hole 131a. Hence, when the probe 77 is inserted into the rotary ring 131, the leaf spring 141 pushes the probe 77 toward the hand piece 72. This makes it easy to set the male screw 132, i.e., the proximal end portion of the probe 77, into the screw hole 133 made in the distal end portion of the horn 74.

Figure 24:
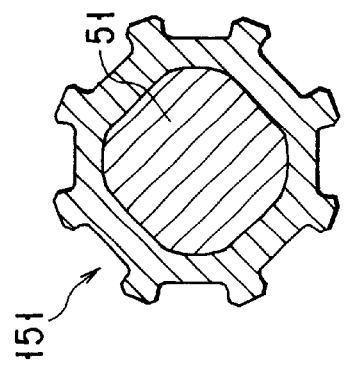
FIG. 24 is a sectional view, taken along line 24—24 in FIG. 23.
Figure 23:
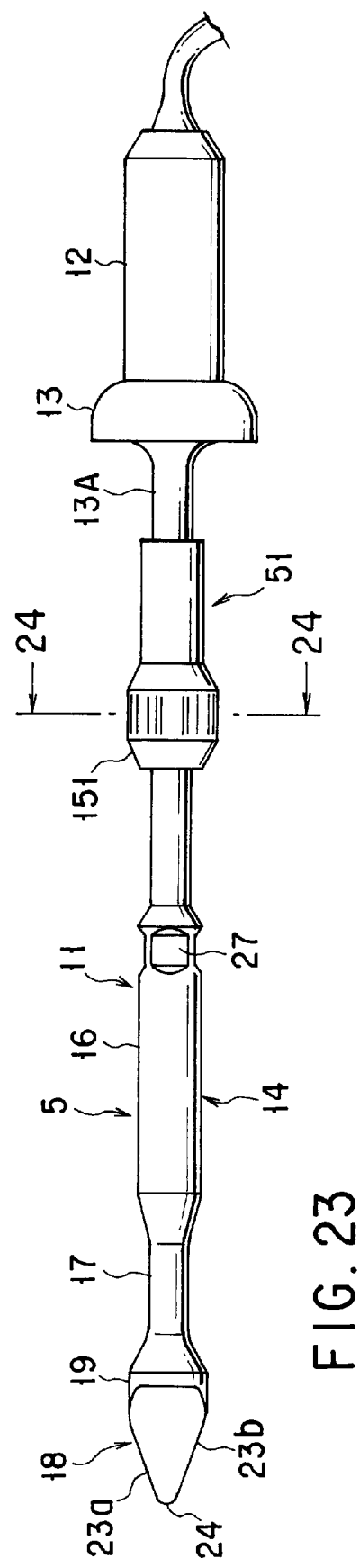
FIG. 23 is a front view of the needle unit of an ultrasonic trocar, which is the eighteenth embodiment of the invention.

FIGS. 23 and 24 illustrates the needle unit of an ultrasonic trocar, which is the eighteenth embodiment of the invention.

The needle unit is a modification of the needle unit 5 of the ultrasonic trocar according to the fifth embodiment (FIG. 7).

As shown in FIG. 23, the probe 11 and the grip section 13 are connected together by a connection probe 51. The connection probe 51 is located at a node of the ultrasonic wave. The connection probe 51 has a wrench section 151 that is similar in shape to the torque-generating section 79 of the fourteenth embodiment (FIGS. 19A to 19C). The wrench section 151 is made of plastic, such as PEEK (Polyetherethyle-ketone), PTFE (Teflon) or PsF (Polysulfone).

The maximum diameter of the wrench section 151 is equal to or smaller than the maximum diameter of the paracentetic section 18 of the needle unit 5. The trocar 1 can therefore be smoothly inserted into the tubular sheath 4.

In the eighteenth embodiment, tubular sheath 4 having different diameters can be interchangeably used. Whenever the sheath 4 is replaced with another, the needle unit 5 must be replaced with another. To be replaced with another, the needle unit 5 must be disconnected from the horn 13A of the hand piece 12. The needle unit 5 must be disconnected from the hand piece 12, also to be washed or stored away. To disconnect the unit 5 from the horn 13A, the doctor only need to hold and rotate the wrench section 151 with fingers. To secure the unit 5 to the horn 13A appropriately, too, it suffices to hold the wrench section 151 with fingers and rotate the section 151 in the opposite direction.

The needle unit 5 has two diametrically opposing flat surfaces 27. It is at these flat surfaces 27 that the needle unit 5 can be held with a tool such as a spanner or the like. It may become impossible to rotate the wrench section 151 to adjust the torque because the needle unit 5 has been secured to the horn 13A, too firmly and tightly due to the ultrasonic vibration. In this case, the probe 11 is held with a spanner or the like, at the flat surfaces 27 and rotated to remove the needle unit 5 from the horn 13A of the hand piece 12.

FIG. 25 is a side view of the needle unit 5 of an ultrasonic trocar, which is the nineteenth embodiment of the invention. The needle unit 5 is a modification of the needle unit 5 of the eighteenth embodiment (FIGS. 23 and 24).

As shown in FIG. 25, the wrench section 151 of the needle unit 5 has flat surfaces 152. At these flat surfaces 152, the probe 11 is held and rotated with a spanner or the like.

The flat surfaces 152 may be provided at any part of the needle unit 5. However, if the surfaces 152 are provided at a position other than a node of the ultrasonic wave and that part of the unit 5 which has the surfaces 152 is deformed when held with a spanner, the needle unit 5 may fail to vibrate in desired manner. In view of this it required that the flat surfaces 152 be formed on the wrench section 151, because the wrench section 151 is located at a node of the ultrasonic wave.

The flat surfaces 152 are therefore formed on the wrench section 151 in the nineteenth embodiment. If the wrench section 151 cannot be rotated with hand in either direction, the wrench section 151 may be held with a wrench at the flat surfaces 152 and may be rotated by the use of the spanner. In addition, it is easy for anyone using the ultrasonic trocar to know where the flat surfaces 152 are provided. It is because he or she often holds and rotate the wrench section 151 with fingers to secure or remove the needle unit 5 to or from the horn 13A and because the surfaces 152 are formed on the wrench section 151.

FIG. 26 illustrates an ultrasonic trocar according to the twentieth embodiment of the invention.

The twentieth embodiment is a modification of the first embodiment (FIGS. 1A and 1B, FIG. 2, and FIGS. 3A to 3D).

As shown in FIG. 26, the tubular sheath 4 contains a flap valve 161 and a spring 162. The spring 163 pushes the flap valve 161 onto the needle unit 5.

As the needle unit 5 is inserted into the tubular sheath 4, the flap valve 161 contacts the circumferential surface of the wrench section 151 of the needle unit 5, which is located at a node of the ultrasonic wave.

In an ordinary trocar, the flap valve contacts the needle unit as the needle unit is inserted into the tubular sheath 4. In an ultrasonic trocar, the needle unit moves in frictional contact with the flap valve while undergoing ultrasonic vibration, inevitably making noise and forming wear dust. To make matters worse, the interface between the needle unit and the flap valve hinders the ultrasonic vibration of the needle unit.

In the ultrasonic trocar according to the twentieth embodiment of the invention, the interface between the needle unit 5 and the flap valve 161 does not hinder the ultrasonic vibration of the needle unit 5. This is because the wrench section 151 of the needle unit 5 is located at the node of ultrasonic vibration of the needle unit 5, and also because the flap valve 161 contacts the circumferential surface of the wrench section 151.

The present invention is not limited to the embodiments described above. Various changes and modifications can of course be made, without departing from the scope and spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic trocar comprising:
 a tubular sheath; and
 a needle unit inserted in the tubular sheath and adapted to penetrate an abdominal wall while being vibrated with ultrasonic waves;
 wherein the needle unit includes, at a distal end thereof, a substantially pyramidal paracentetic section which is a thickest part of the needle unit; and
 wherein the paracentetic section includes: (i) two cutting surfaces formed by cutting two diagonally opposing first ridges, each of the two cutting surfaces being smoothly curved, and (ii) two sharp cutting edges for cutting living tissues, the two sharp cutting edges being formed at two diagonally opposing second ridges and being positioned symmetrically with respect to an axis of the needle unit.

2. The ultrasonic trocar according to claim 1, wherein the tubular sheath includes an insertion passage in which the needle unit is inserted, and a valve for enabling the insertion passage to be blocked, and wherein the needle unit includes a contact-preventing member located near a node of an ultrasonic wave for preventing the valve and the needle unit from coming into direct contact with each other.

3. An ultrasonic trocar comprising:
 a tubular sheath; and
 a needle unit inserted in the tubular sheath and adapted to penetrate an abdominal wall while being vibrated with ultrasonic waves;
 wherein the needle unit includes, at a distal end thereof, a substantially pyramidal paracentetic section which is a thickest part of the needle unit; and wherein the paracentetic section includes a maximum diameter portion having a diameter of at least 3 mm, two cutting surfaces formed by cutting two diagonally opposing first ridges, and two sharp cutting edges for cutting living tissues, the two sharp cutting edges being formed at two diagonally opposing second ridges and being positioned symmetrically with respect to an axis of the needle unit.

4. An ultrasonic trocar comprising:

a tubular sheath; and a needle unit inserted in the tubular sheath and adapted to penetrate an abdominal wall while being vibrated with ultrasonic waves;

wherein the needle unit includes, at a distal end thereof, a substantially pyramidal paracentetic section which is a thickest part of the needle unit; and wherein the paracentetic section includes two cutting surfaces formed by cutting two diagonally opposing first ridges, and three sharp cutting edges for cutting living tissues, two of the three sharp cutting edges being formed at two diagonally opposing second ridges and being disposed close to a maximum diameter portion of the paracentetic section symmetrically with respect to an axis of the needle unit, and the other one of the three sharp cutting edges being formed at a minimum diameter portion of the paracentetic section.

5. An ultrasonic trocar comprising:

a tubular sheath; and a needle unit inserted in the tubular sheath and adapted to penetrate an abdominal wall while being vibrated with ultrasonic waves;

wherein the needle unit includes, at a distal end thereof, a substantially pyramidal paracentetic section which is a thickest part of the needle unit; and wherein the paracentetic section includes a rounded distal end portion having a sharp tip having an acute apex angle, two cutting surfaces formed by cutting two diagonally opposing first ridges, and two sharp cutting edges for cutting living tissues, the two sharp cutting edges being formed at two diagonally opposing second ridges and being positioned symmetrically with respect to an axis of the needle unit.

6. The ultrasonic trocar according to claim 5, wherein the rounded distal end portion has a maximum radius of curvature of about 3 mm, and the acute apex angle of the sharp tip ranges from about 45° to about 90°.

7. An ultrasonic trocar comprising:

a tubular sheath; and a needle unit inserted in the tubular sheath and adapted to penetrate an abdominal wall while being vibrated with ultrasonic waves;

wherein the needle unit includes, at a distal end thereof, a substantially pyramidal paracentetic section which is a thickest part of the needle unit; and wherein the paracentetic section includes a needle-shaped projection protruding from a distal end thereof, two cutting surfaces formed by cutting two diagonally opposing first ridges, and two sharp cutting edges for cutting living tissues, the two sharp cutting edges being formed at two diagonally opposing second ridges and being positioned symmetrically with respect to an axis of the needle unit.

8. An ultrasonic trocar comprising:

a tubular sheath; and a needle unit inserted in the tubular sheath and adapted to penetrate an abdominal wall while being vibrated with ultrasonic waves;

wherein the needle unit includes, at a distal end thereof, a substantially pyramidal paracentetic section which is a thickest part of the needle unit;

wherein the paracentetic section includes two cutting surfaces formed by cutting two diagonally opposing first ridges, and two sharp cutting edges for cutting living tissues, the two sharp cutting edges being formed at two diagonally opposing second ridges and being positioned symmetrically with respect to an axis of the needle unit;

wherein the tubular sheath includes an insertion section adapted to penetrate the abdominal wall, together with the needle unit, and two projections extending from a distal end of the insertion section to be set in engagement with the needle unit; and wherein the needle unit includes engagement grooves cut in a maximum diameter portion of the paracentetic section to hold the projections of the insertion section when the needle unit penetrates the abdominal wall.

9. An ultrasonic trocar comprising:

a tubular sheath; and a needle unit inserted in the tubular sheath and adapted to penetrate an abdominal wall while being vibrated with ultrasonic waves;

wherein the needle unit is coated, at least at a distal part thereof, with a layer which increases wear-resistance and surface strength of the needle unit;

wherein the needle unit includes, at a distal end thereof, a substantially pyramidal paracentetic section which is a thickest part of the needle unit; and wherein the paracentetic section includes two cutting surfaces formed by cutting two diagonally opposing first ridges, and two sharp cutting edges for cutting living tissues, the two sharp cutting edges being formed at two diagonally opposing second ridges and being positioned symmetrically with respect to an axis of the needle unit.

10. An ultrasonic trocar comprising:

a tubular sheath;

a probe inserted in the tubular sheath and adapted to penetrate a living tissue;

two ridges formed on a distal end portion of the probe, the two ridges being located symmetrically with respect to an axis of the probe and being smoothly coupled at a tip portion of the distal end portion; and two smoothly curved cutting surfaces formed on the distal end portion of the probe, the two cutting surfaces being defined by the two ridges and also being located symmetrically with respect to the axis of the probe.

11. The ultrasonic trocar according to claim 10, wherein the distal end portion of the probe has a substantially conical shape.

12. The ultrasonic trocar according to claim 11, further comprising a cutting edge formed at the tip portion of the distal end portion.

13. The ultrasonic trocar according to claim 11, further comprising a first cutting edge formed on a first one of the two ridges, and a second cutting edge formed on a second one of the two ridges.

14. The ultrasonic trocar according to claim 13, further comprising a third cutting edge formed at the tip portion of the distal end portion.

15. The ultrasonic trocar according to claim 13, wherein the first and second cutting edges are formed at a maximum diameter position of the distal end portion of the probe.

16. The ultrasonic trocar according to claim 10, further comprising a first cutting edge formed on a first one of the two ridges, and a second cutting edge formed on a second one of the two ridges.

17. The ultrasonic trocar according to claim 16, further comprising a third cutting edge formed at the tip portion of the distal end portion.

18. The ultrasonic trocar according to claim 16, wherein the first and second cutting edges are formed at a maximum diameter position of the distal end portion of the probe.

19. The ultrasonic trocar according to claim 10, further comprising a cutting edge formed at the tip portion of the distal end portion.

20. The ultrasonic trocar according to claim 10, wherein the tubular sheath includes an insertion passage in which the probe is inserted, and a valve for enabling the insertion passage to be blocked, and wherein the probe includes a contact-preventing member located near a node of an ultrasonic wave for preventing the valve and the probe from coming into direct contact with each other.

21. An ultrasonic trocar comprising:
   a tubular sheath;
   a probe inserted in the tubular sheath and adapted to penetrate a living tissue;
   two ridges formed on a distal end portion of the probe, the two ridges being located symmetrically with respect to an axis of the probe and being smoothly coupled at a tip portion of the distal end portion;
   two smoothly curved cutting surfaces formed on the distal end portion of the probe, the two cutting surfaces being defined by the two ridges and also being located symmetrically with respect to the axis of the probe; and
   a sharp tip portion formed by distal end portions of the two cutting surfaces, wherein the sharp tip portion has an acute angle.

22. The ultrasonic trocar according to claim 21, wherein the acute angle of the sharp tip portion ranges from about 45° to about 90°.

* * * * *

UNITED STATES PATENT AND TRADEMARK OFFICE
CERTIFICATE OF CORRECTION

PATENT NO.     : 6,497,714 B1                                            Page 1 of 1
DATED          : December 24, 2002
INVENTOR(S)    : Manabu Ishikawa It is certified that error appears in the above-identified patent and that said Letters Patent is hereby corrected as shown below:

<u>Title page,</u>
Item [75], Inventors, delete "Mitsumasa Okada, both"

Signed and Sealed this

Twenty-ninth Day of July, 2003

JAMES E. ROGAN
*Director of the United States Patent and Trademark Office*